United States Patent
Kroll et al.

(10) Patent No.: US 7,164,944 B1
(45) Date of Patent: Jan. 16, 2007

(54) ANALGESIC THERAPY FOR ICD PATIENTS

(75) Inventors: Mark W. Kroll, Simi Valley, CA (US); Eric Falkenberg, Simi Valley, CA (US); Paul A. Levine, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 518 days.

(21) Appl. No.: 10/417,477

(22) Filed: Apr. 15, 2003

(51) Int. Cl.
*A61N 1/00* (2006.01)

(52) U.S. Cl. .................. 607/2; 607/4; 607/5; 607/46
(58) Field of Classification Search .......... 607/4–7, 607/43, 46; 128/907
See application file for complete search history.

(56) References Cited

U.S. PATENT DOCUMENTS

| | | | |
|---|---|---|---|
| 4,712,555 A | 12/1987 | Thornander et al. | 128/419 PG |
| 4,788,980 A | 12/1988 | Mann et al. | 128/419 PG |
| 4,940,052 A | 7/1990 | Mann et al. | 128/419 PG |
| 4,944,298 A | 7/1990 | Sholder | 128/419 PG |
| 5,466,254 A | 11/1995 | Helland | 607/123 |
| 5,476,483 A | 12/1995 | Bornzin et al. | 607/17 |
| 5,782,882 A * | 7/1998 | Lerman et al. | 607/10 |
| 5,792,187 A * | 8/1998 | Adams | 607/5 |
| 5,836,971 A * | 11/1998 | Starkweather | 607/4 |
| 5,893,881 A * | 4/1999 | Elsberry et al. | 607/5 |
| 6,058,328 A * | 5/2000 | Levine et al. | 607/14 |
| 6,091,989 A | 7/2000 | Swerdlow et al. | 607/5 |
| 6,154,672 A * | 11/2000 | Pendekanti et al. | 607/5 |
| 6,167,305 A | 12/2000 | Cammilli et al. | 607/5 |
| 6,292,694 B1 | 9/2001 | Schloss et al. | 607/9 |
| 6,314,323 B1 | 11/2001 | Ekwall | 607/23 |
| 6,438,418 B1 | 8/2002 | Swerdlow et al. | 607/5 |
| 6,650,936 B1 * | 11/2003 | Sullivan et al. | 607/6 |

\* cited by examiner

*Primary Examiner*—Robert E. Pezzuto
*Assistant Examiner*—Brian T. Gedeon

(57) ABSTRACT

An exemplary method includes delivering a therapy selected from tiered therapies that include cardioversion and/or defibrillation therapies wherein the delivered therapy aims to treat a cardiac condition, delivering analgesic stimulation, determining whether the delivered therapy successfully treated the cardiac condition, and responsive to the determining, changing one or more analgesic stimulation parameters. Various other exemplary methods and/or devices capable of performing such methods are also disclosed.

27 Claims, 8 Drawing Sheets

ANALGESIC THERAPY FOR ICD PATIENTS

RELATED APPLICATIONS

This application is related to copending U.S. patent application Ser. No. 10/392,619, filed Mar. 19, 2003, titled "Pacing Therapy and Acupuncture."

TECHNICAL FIELD

Exemplary methods and/or devices presented herein generally relate to cardiac pacing and/or stimulation therapy. Various exemplary methods and/or devices concern delivery of analgesic therapy in a patient subject to pacing, antitachycardia pacing (ATP), cardioversion and/or defibrillation.

BACKGROUND

Implantable cardioverter defibrillators (ICDs) have traditionally been used in patients who survived, or have a high risk of experiencing, a sudden cardiac death event. More recently, indications have been expanded to include patients who have had asymptomatic nonsustained ventricular tachycardia, for example, with decreased ventricular function.

A typical ICD has one or more electrodes for delivering defibrillation shocks to a patient's heart. An ICD may use such electrodes, for example, upon detection of a ventricular tachycardia or a ventricular fibrillation. In general, after the ICD determines a need for a shock, a delay typically occurs wherein the ICD charges a shock capacitor. The ICD then discharges the capacitor to deliver a shock, typically of approximately 25 J. An ICD device may also repeat the charge and discharge cycle (e.g., for approximately 5 cycles). Other ICD devices may provide programmable low-energy cardioversion in addition to or in lieu of high-energy shocks. Yet other ICD devices provide a feature that is commonly referred to as "tiered therapy", which typically includes antitachycardia pacing for painless (or relatively painless) termination of monomorphic ventricular tachycardias, programmable low-energy cardioversion, high-energy defibrillation, and backup bradycardia pacing.

To determine a need for a shock, an ICD typically has a lead placed in a patient's right ventricle where it provides for sensing of ventricular rate and/or other information for detection of abnormal cardiac behavior. Some ICD systems also include an atrial lead, which can, for example, be used to sense atrial information, to pace and/or to deliver other therapy. In general, an ICD having both atrial and ventricular leads is referred to as a dual-chamber ICD. Yet further, some ICDs and other implantable cardiac therapy devices have one or more electrodes capable of delivering an atrial shock. Hence, such devices may provide for atrial tiered therapy.

While various aforementioned ICDs or other devices may provide for more favorable outcomes, shock is often associated with patient pain and discomfort. A variety of approaches to alleviating and/or minimizing such pain and discomfort have been reported. One approach involves transcutaneous electrical nerve stimulation (TENS) for blocking transmission of sensory signals (e.g., sensory nerve blockade), another approach involves direct cerebral cortical stimulation, while yet another approach involves direct spinal cord stimulation (SCS). These approaches elicit such stimulation only after determination of a need for a shock and just prior to or in conjunction with delivery of the shock. Hence, for the any significant relief of shock-associated pain or discomfort, the analgesic effect of the stimulation should be nearly instantaneous.

For SCS, the reported analgesic effect is apparently immediate and due to inhibition of impulse transmission in small fiber afferents by activation of large fiber afferents on the associated spinal segmental level. However, other forms of nerve stimulation may have a time delay before production of any significant analgesia. Hence, methods that rely on delivery of analgesic stimulation just prior to or in conjunction with shock delivery may be suboptimal in reducing patient pain or discomfort.

Various exemplary methods, devices and/or systems presented herein aim to reduce or eliminate patient pain or discomfort via analgesic stimulation. In particular, several exemplary methods provide for analgesic stimulation in conjunction with levels of tiered therapy.

SUMMARY

An exemplary method includes delivering analgesic stimulation and a first antitachycardia therapy to a patient, determining whether the first antitachycardia therapy successfully treated the cardiac condition, and delivering analgesic stimulation and a second antitachycardia therapy to the patient if the first antitachycardia therapy failed to treat the cardiac condition, where the second antitachycardia therapy is different from the first antitachycardia therapy.

Various exemplary devices for performing such exemplary method are also disclosed herein along with a variety of other exemplary methods and/or devices. In general, the various devices and methods described herein, and equivalents thereof, are suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

BRIEF DESCRIPTION OF THE DRAWINGS

Features and advantages of the described implementations can be more readily understood by reference to the following description taken in conjunction with the accompanying drawings.

Figure 1:
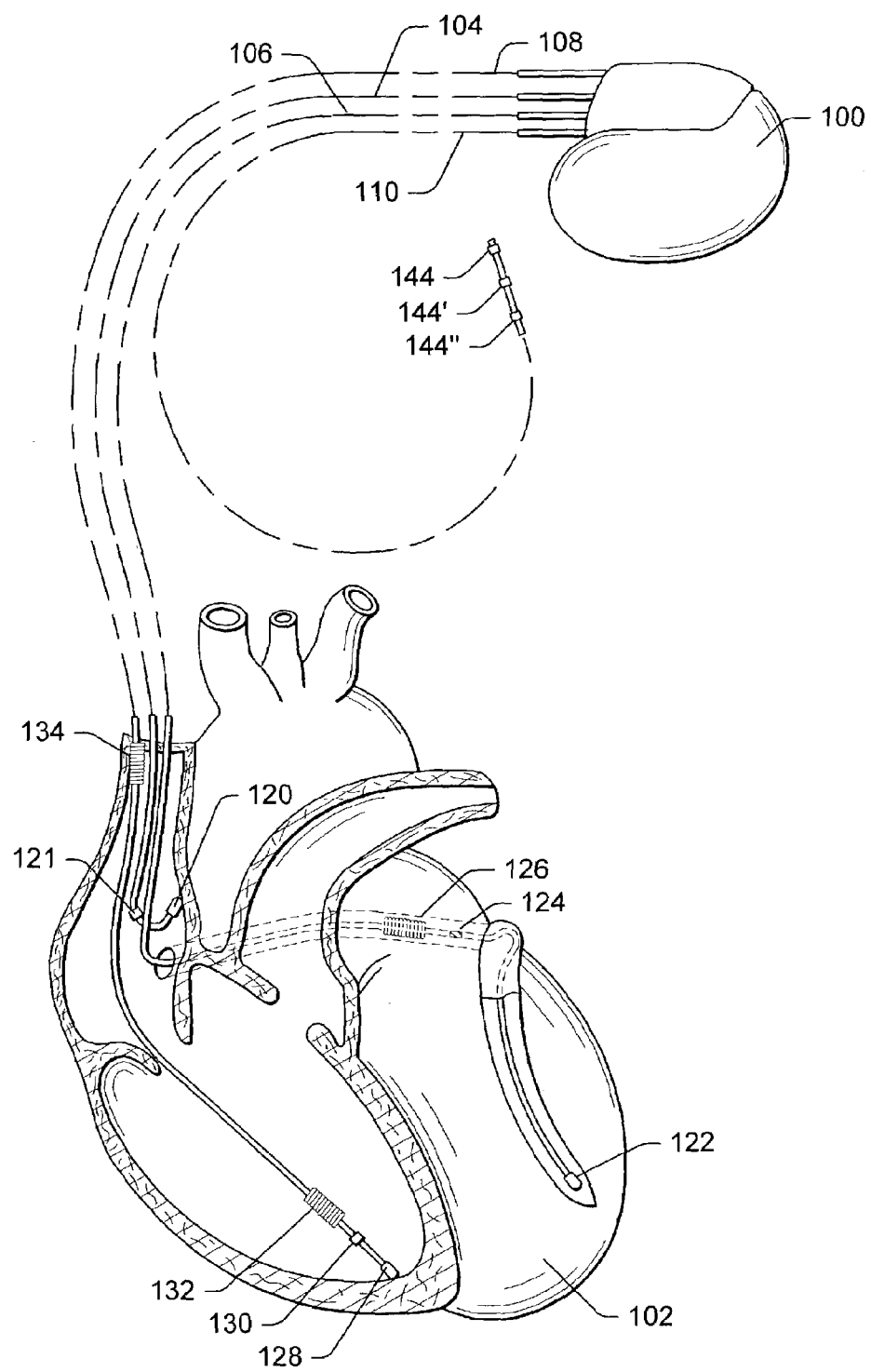

FIG. 1 is a simplified diagram illustrating an exemplary implantable stimulation device in electrical communication with at least three leads implanted into a patient's heart and at least one other lead for delivering stimulation and/or shock therapy.

Figure 2:
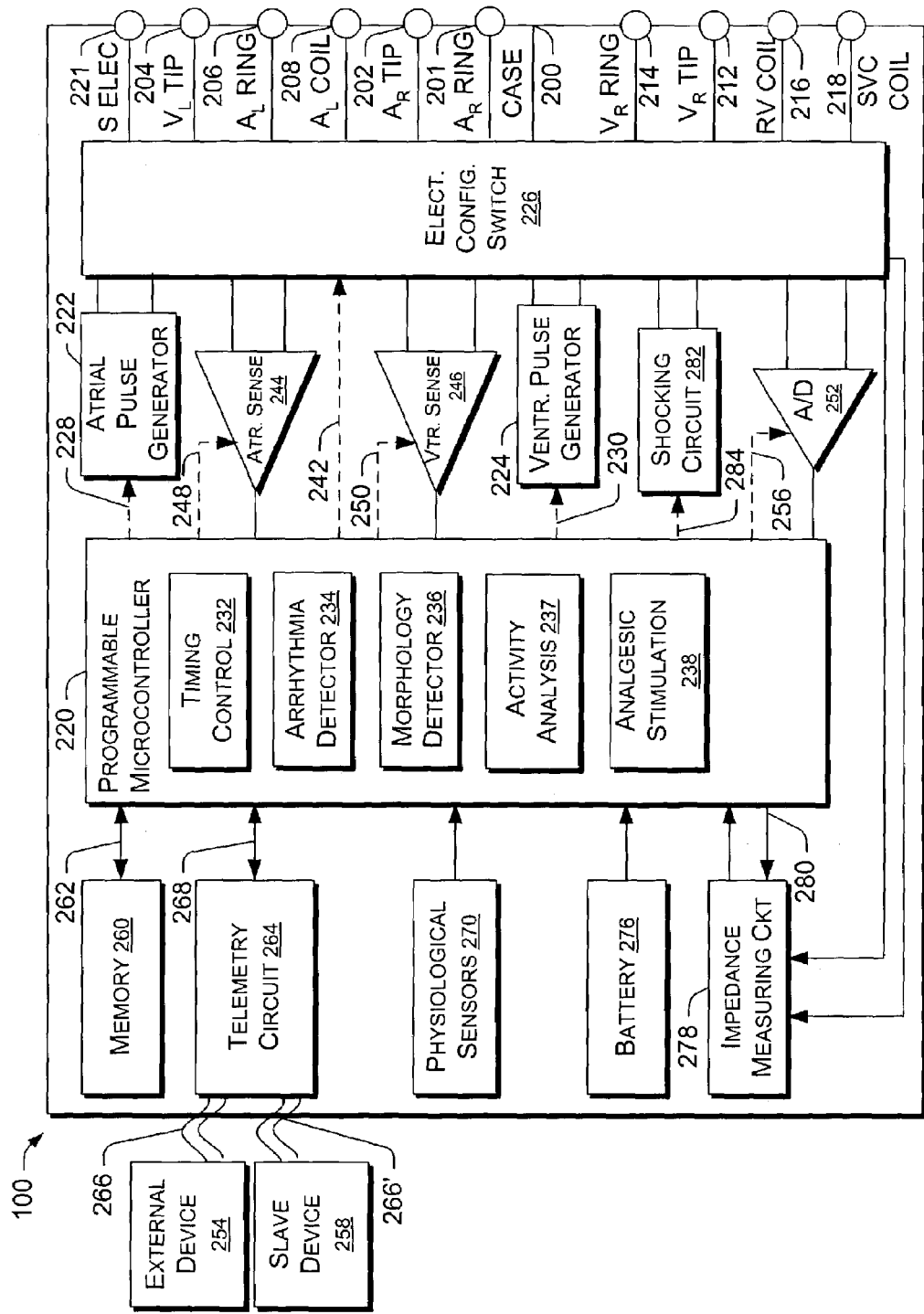

FIG. 2 is a functional block diagram of an exemplary implantable stimulation device illustrating basic elements that are configured to provide cardioversion, defibrillation, pacing stimulation, autonomic nerve stimulation or other tissue and/or nerve stimulation. The implantable stimulation device is further configured to sense information and administer stimulation pulses responsive to such information.

Figure 3:
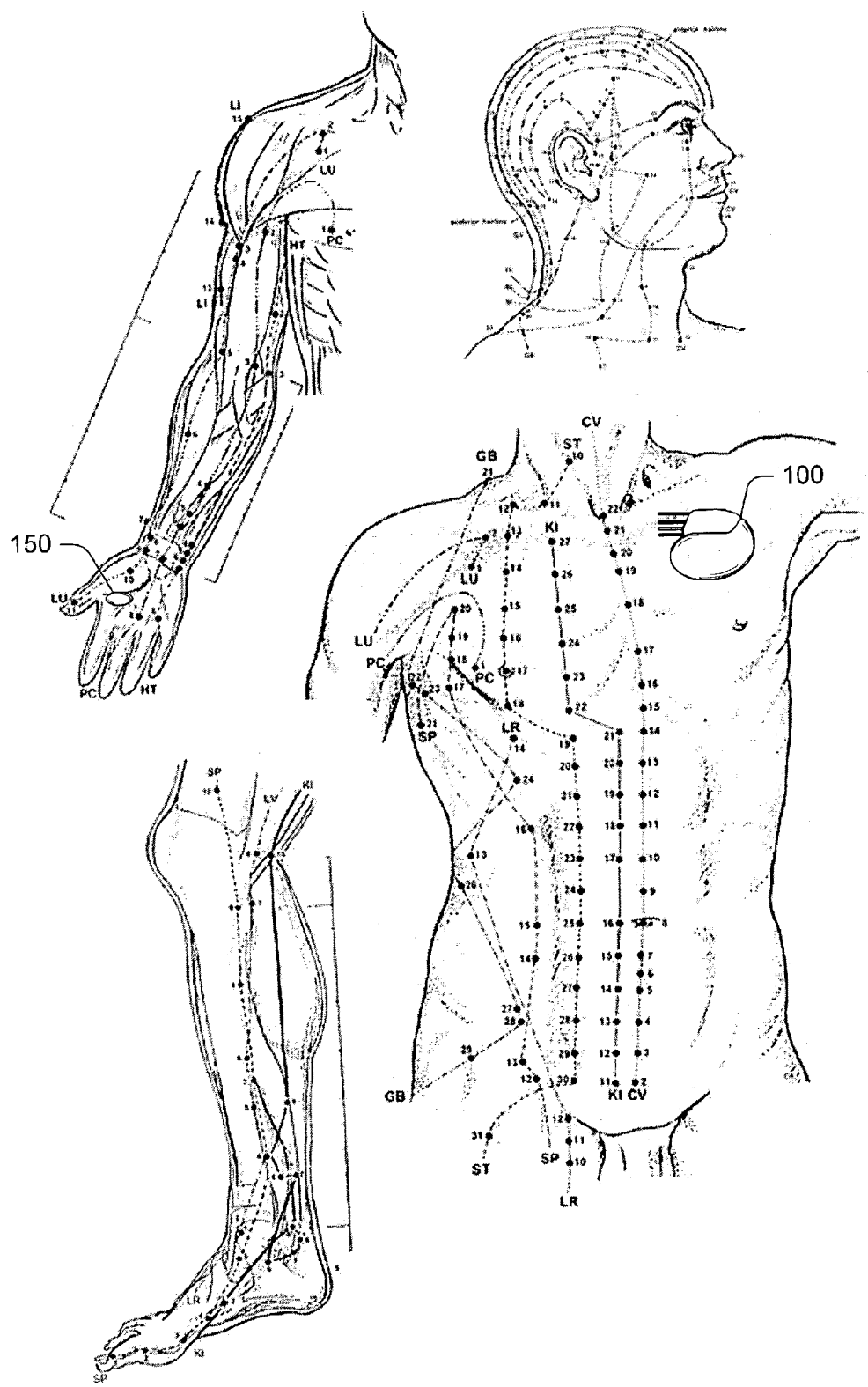

FIG. 3 is an approximate anatomical diagram including an ICD and a slave device.

Figure 4:
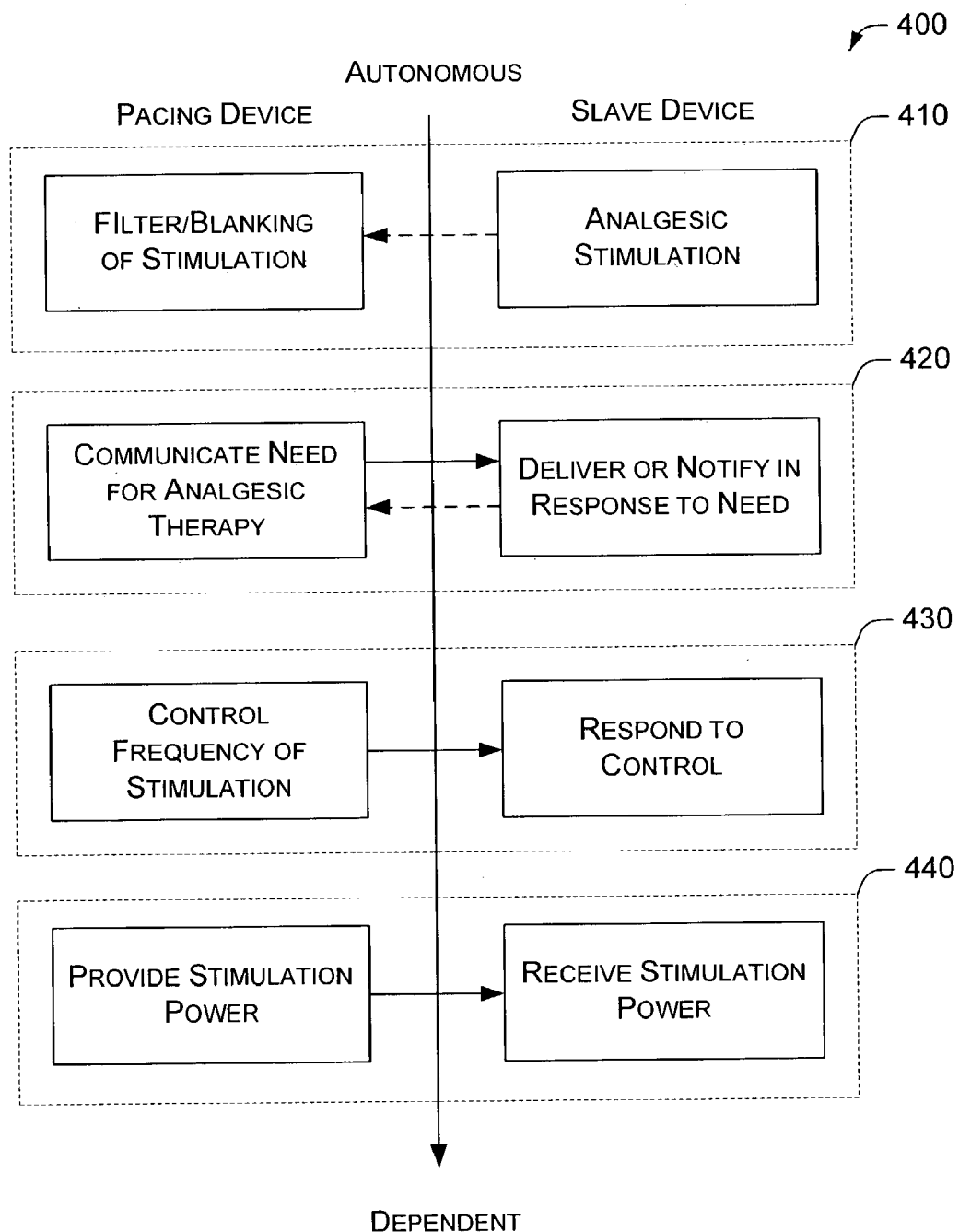

FIG. 4 is an exemplary spectrum showing exemplary relationships between an ICD and a slave device.

Figure 5:
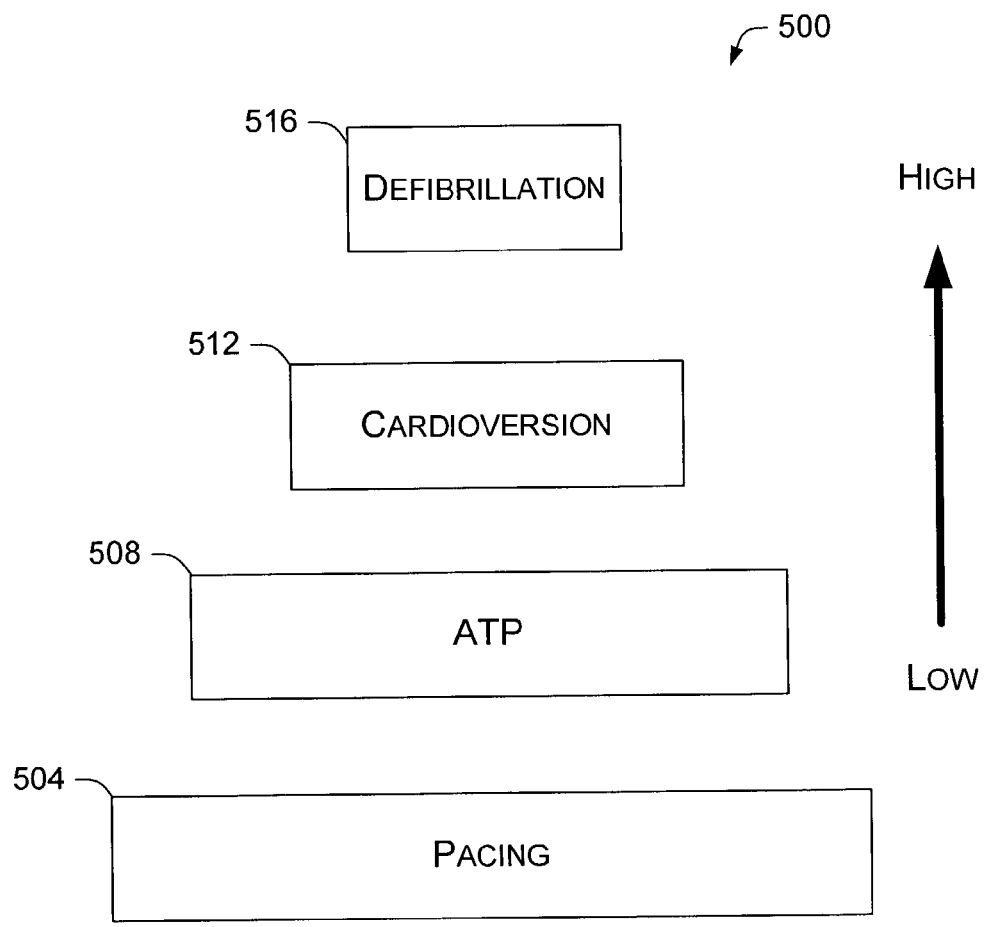

FIG. 5 is a diagram of various exemplary tiers of therapy.

Figure 6:
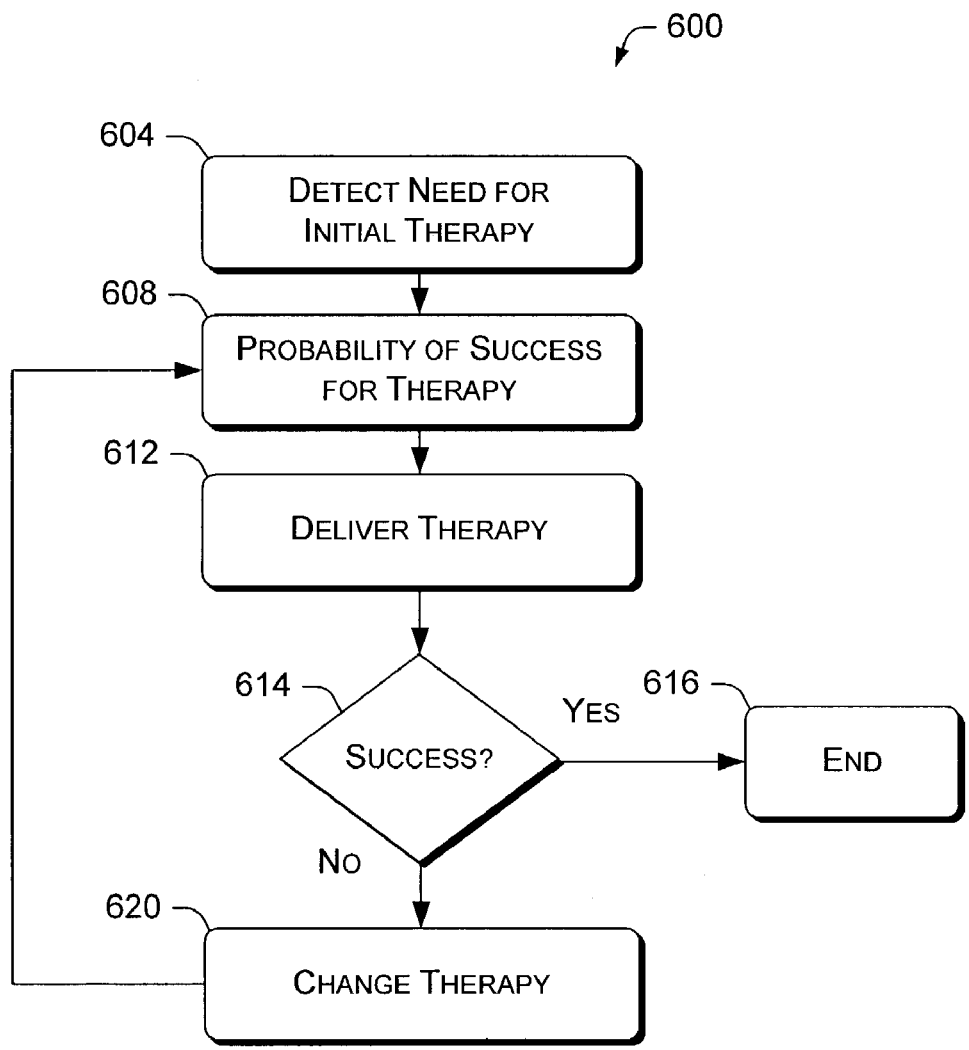

FIG. 6 is a flow diagram of an exemplary method for delivering one or more therapies and assigning or associating a probability with a therapy.

Figure 7:
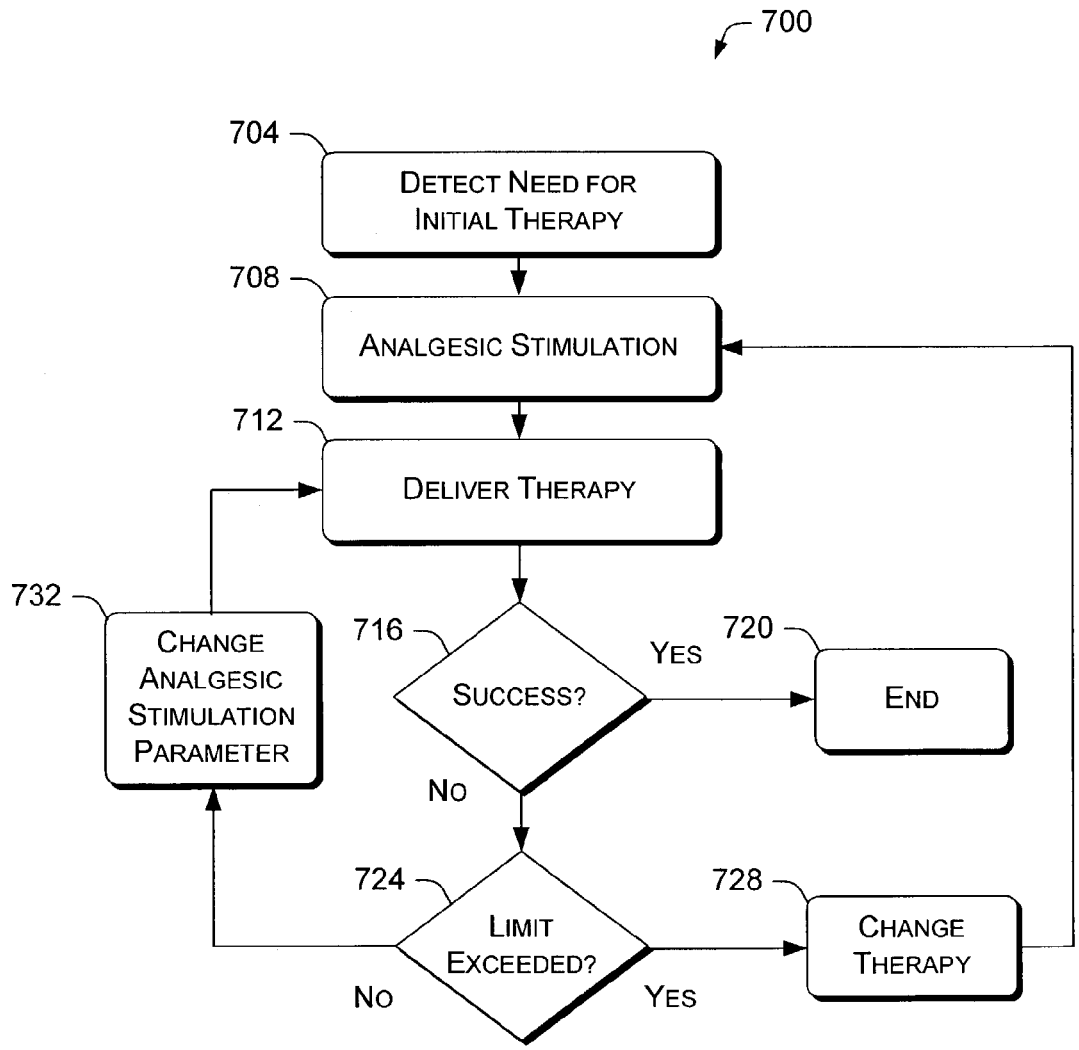

FIG. 7 is a flow diagram of an exemplary method for delivering one or more therapies and delivering analgesic stimulation.

Figure 8:
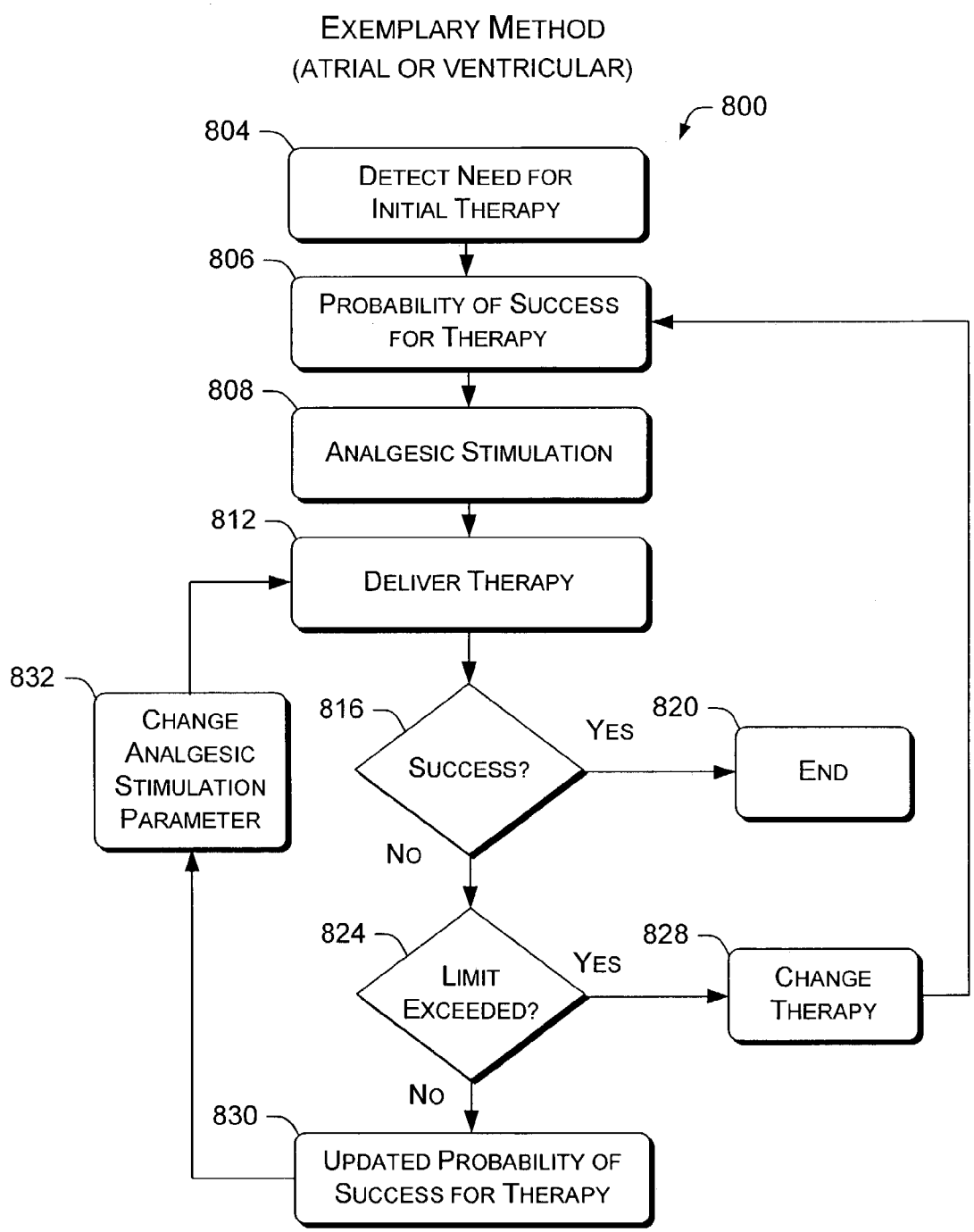

FIG. 8 is a flow diagram of an exemplary method for delivering one or more therapies and delivering analgesic stimulation.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Overview

Various exemplary methods, devices and/or systems described herein rely on analgesic stimulation to reduce or alleviate pain or discomfort associated with cardioversion or defibrillation shocks. An exemplary ICD device is described, followed by a description of various forms of analgesic stimulation. Tiered therapies are then presented followed by exemplary methods of analgesic stimulation and exemplary analgesic stimulation devices.

Exemplary ICD

Various exemplary methods described below are intended to be implemented in connection with any stimulation device that is configured or configurable to stimulate nerves and/or stimulate and/or shock a patient's heart.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of analgesic stimulation pulses. In addition, the device 100 includes a fourth lead 110 having, in this implementation, three electrodes 144, 144', 144" suitable for analgesic stimulation. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for analgesic stimulation.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. patent application Ser. No. 09/457,277, filed Dec. 8, 1999, entitled "A Self-Anchoring, Steerable Coronary Sinus Lead" (Pianca et al.); and U.S. Pat. No. 5,466,254, "Coronary Sinus Lead with Atrial Sensing Capability" (Helland), which are incorporated herein by reference.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal ($A_R$ TIP) 202 adapted for connection to the atrial tip electrode 120. A right atrial ring terminal ($A_R$ RING) 201 is also shown, which is; adapted for connection to the atrial ring electrode 121. To achieve left chamber sensing, pacing, and/or shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively.

To support right chamber sensing, pacing, and/or shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals used within the stimulation device and their interrelationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or for analgesic stimulation) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes an atrial activity analysis module 237. The atrial activity analysis module 237 optionally implements one or more methods for sensing, information analysis, and/or stimulation control related to atrial activity. For example, the atrial activity analysis module 237 optionally implements one or more of the exemplary methods described below.

Microcontroller 220 further includes an analgesic stimulation module 238 for performing a variety of tasks related to analgesic stimulation, including blanking, filtering, etc. of signals related to analgesic stimulation. This component can be utilized by the stimulation device 100 for determining desirable times to administer various therapies. The analgesic module 238 may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. Further, such filtering is optionally pre-programmed, pre-selected and/or programmable to address interference stemming from analgesic stimulation. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., pacing, bradycardia pacing, anti-tachycardia pacing, cardioversion shocks or defibrillation shocks, collectively referred to as "tiered therapy" and described in more detail below).

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The telemetry circuit 264 is optionally in telemetric communication via the communication link 266' with a slave device 258. The slave device 258 may be internal (i.e., at least partially implanted in a patient) or external. As described in more detail below, various slave devices have an ability to deliver an analgesic stimulus while other slave devices signal a user to administer analgesic therapy and/or other therapy. Communication between the exemplary device 100 and the slave device 258 may occur in bidirectional and/or unidirectional manner.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V—V Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

The impedance measuring circuit 278 optionally measures impedance at or near an acupoint or other analgesic stimulation point or region. For example, an electrode may have impedance that varies with its position in relation to an acupoint. Thus, the impedance measuring circuit 278 may detect when an electrode is properly or improperly positioned with respect to an acupoint. Such a circuit may aid in the positioning of an electrode for analgesic stimulation.

In the case where the stimulation device 100 is intended to operate as an implantable cardioverter/defibrillator (ICD) device, it may detect an occurrence of an arrhythmia, and automatically apply an appropriate therapy to the heart aimed at terminating the detected arrhythmia (see also tiered therapies below). To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this exemplary ICD, may be selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocking pulses are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Exemplary Implantable Cardiac Therapy Device and Analgesic Stimulator

Referring to FIG. 3, an exemplary ICD 100 and an analgesic stimulator 150 are shown along with various diagrams of the human body. In this example, the ICD 100 is implanted in a patient's chest and the analgesic stimulator 150 is positioned at the patient's hand (e.g., at or near an acupoint). The analgesic stimulator 150 optionally operates independent of the ICD 100 or operates in a manner that depends on the ICD 100. In the latter instance, the analgesic stimulator 150 may simply include one or more electrodes on a lead connected to the ICD 100. In general, the analgesic stimulator 150 is not limited in size and it is positionable at or near an analgesic stimulation point or region and capable of stimulation at or near such point or region. Further, the analgesic stimulator 150 may operate as a slave device (see, e.g., the slave device 258 of FIG. 2). As a slave device, the analgesic stimulator 150 may receive telemetric commands communicated from the ICD device 100. The analgesic stimulator 150 may alternatively, or in addition to, communicate information to the ICD device 100. Thus, the exemplary analgesic stimulator 150 may communicate in a unidirectional or bidirectional manner with the exemplary ICD device 100. Yet further, as already mentioned, an ICD device may communicate with a slave device that simply notifies a patient to administer analgesic stimulation.

Referring to FIG. 4, an exemplary spectrum 400 ranging from autonomous to dependent is shown to describe possible relationships between an ICD and a slave device (e.g., notification device, analgesic stimulator, etc.). In a first scenario 410, an ICD includes appropriate circuitry to operate properly regardless of electromagnetic interference generated by electroacupuncture, TENS, SCS, etc., while a slave device (e.g., an electroacupuncture stimulator, TENS stimulator, SCS stimulator, etc.) operates independent of the ICD. In this scenario, the slave device optionally transmits a code to the ICD to notify the ICD of an impending stimulation session. For example, an exemplary slave device may include one or more sensors (e.g., physiology sensors) or receive input from a user or from one or more sensors. Such a slave device can determine when stimulation is desired and transmit a code an ICD. Alternatively, the ICD may sense such stimulation and respond appropriately, for example, based on magnitude and frequency of the applied stimulation. In this alternative, the ICD device only requires an ability to recognize such stimulation; thus, the slave device and ICD device are quite independent.

In a second scenario 420, an ICD detects a need for analgesic stimulation and communicates the need. For example, an ICD may detect a need for acupuncture or other analgesic therapy and then communicate information about the need to a slave device. In response, the slave device may delivery and/or notify in response to the communicated information. In general, the information calls for administration of acupuncture or other analgesic therapy. For example, where the slave device is capable of administering such therapy, the slave device would receive the communicated information and respond accordingly. According to this example, the slave device may include a power supply and circuitry capable of responding to communicated information from the ICD wherein the responding includes delivery of analgesic stimulation by the slave device. Alternatively, a slave device may notify a patient to administer acupuncture or other analgesic therapy.

In a third scenario 430, an ICD includes a frequency or pulse generator that controls stimulation frequency of a slave device (e.g., an electroacupuncture, TENS, SCS, etc.).

For example, the ICD may select a stimulation frequency of approximately 1 Hz to approximately 5 Hz or higher (e.g., 200 Hz or more) depending on need. In this example, the slave device stimulator has a power supply and circuitry capable of responding to the control frequency signal from the ICD. Accordingly, the slave device only needs to respond to the frequency or pulse generator of the ICD device. In this example, the slave device depends on the ICD device to a greater degree that the slave devices of the first scenario 410 and the second scenario 420.

In a fourth scenario 440, an ICD operates as a pulse generator, power supply, etc., for a slave device. According to this exemplary scenario, the slave device includes one or more electrodes that discharge power supplied by the ICD. For example, an ICD device may supply power to a slave device via a lead. Thus, according to this scenario, the slave device is highly dependent on the ICD device. This scenario includes ICD devices having electrode-bearing leads suitable for analgesic stimulation. Further, the electrode-bearing leads may be leads found on traditional ICDs. Thus, the slave device can be one or more electrodes on a lead, or a self-contained device such as device 150.

Tiered Therapy

Tiered therapy typically includes one or more schemes that aim to alleviate an abnormal cardiac condition. Traditional tiered therapy includes antitachycardia pacing (ATP), cardioversion and/or defibrillation. As described herein, tiered therapy may also include various forms of pacing, typically as a first tier. Sometimes such first tier pacing includes what is sometimes referred to as "preemptive" pacing. For example, U.S. Pat. No. 6,058,328, entitled "Implantable stimulation device having means for operating in a preemptive pacing mode to prevent tachyarrhythmias and method thereof", to Levine et al., and assigned to Pacesetter, Inc. ('328 patent), discloses preemptive pacing when sensing of one or more conditions suggest that onset of an arrhythmia is imminent. Such conditions may indicate that a change has occurred in a patient's cardiac cycle from a previously-determined normal cardiac cycle. Responsive to such a change, implementation of a preemptive pacing therapy may occur, such as, overdrive pacing, pacing with randomicity, or mode switching. Further, according to the '328 patent, which is incorporated by reference herein, preemptive pacing may be continuous or on demand U.S. Pat. No. 6,292,694, entitled "Implantable medical device having atrial tachyarrhythmia prevention therapy", to Schloss et al., assigned to Pacesetter, Inc. ('694 patent), discloses implementation of pacing upon detection of a condition such as an interatrial conduction disturbance. The '694 patent is incorporated by reference herein.

Various exemplary sensing and/or detection methods of the '328 patent and the '694 patent are suitable for invoking a first tier or higher tier pacing therapy and/or analgesic stimulation. Thus, pacing, as a tier of therapy, and/or analgesic stimulation may be invoked upon occurrence of or a change in one or more conditions. Of course, conditions other than those mentioned in the '328 patent and '694 patent may also be suitable for determining when an appropriate tier of therapy or analgesic stimulation should be applied. For example, an exemplary device may sense atrial repolarization wave (Ta wave), aspects of ventricular repolarization wave (T wave), QT interval, etc., to determine when a condition exists that warrants pacing as a tier of therapy and/or analgesic stimulation.

FIG. 5 shows exemplary tiers of therapy 500 for atrial or ventricular conditions. The tiers include a pacing therapy tier 504, an antitachycardia pacing therapy tier 508, a cardioversion therapy tier 512 and a defibrillation therapy tier 516. Regarding pacing as a first tier (e.g., tier 504), various aforementioned pacing techniques, such as, preemptive pacing, etc., may be suitable depending on cardiac condition(s). Further, a recent study involving ICDs, The Dual Chamber and VVI Implantable Defibrillator (DAVID) Trial, reported that ventricular backup pacing may be preferred to rate-modulated AV universal pacing in a certain group of ICD patients. The DAVID study compared patients having ICDs using ventricular demand pacing (VVI) with backup pacing at 40 bpm to patients having ICDs using rate-modulated AV universal demand pacing (DDDR) with a base rate of 70 bpm and found that the VVI patients had a better clinical outcome. The study noted that outcome might be related to the frequency of right ventricular pacing. Nearly 60% of all ventricular beats were paced in the DDDR patient group compared with 1% in the VVI patient group and outcome appeared to worsen as the percentage of paced beats increased. Hence, for certain ICD patients, pacing schemes that minimize ventricular pacing may provide for improved clinical outcomes.

Thus, in an ICD, a bradycardia pacing scheme (i.e., backup pacing) may be preferred to pacing schemes that rely on some form of modulated or base-rate pacing. In such instances, appropriate pacing may be implemented as a tier of therapy to alleviate abnormal cardiac conditions other than bradycardia. And, if the implemented pacing does not alleviate the condition, then higher tiered therapies (e.g., ATP, cardioversion, defibrillation) may be implemented.

Traditional tiered therapy for abnormal ventricular conditions typically commences once an ICD device detects a ventricular tachycardia or a ventricular fibrillation. Such abnormal ventricular conditions may be life threatening making time of the essence. If time is of the essence, the ICD may respond to such a condition by calling for defibrillation therapy (e.g., tier 516). Defibrillation therapy generally involves a delay wherein the ICD charges a shock capacitor. The ICD then discharges the capacitor to deliver a ventricular shock, typically of approximately 25 J. An ICD device may also repeat the charge and discharge cycle (e.g., for approximately 5 cycles). While an ICD device may reserve defibrillation as a latter tier therapy, it may optionally use defibrillation as a first-tier therapy for ventricular fibrillation. In general, an ICD device does not synchronize defibrillation therapy with any given portion of an ECG. Again, defibrillation therapy typically involves moderate to high-energy shocks (e.g., 5 J to 40 J), which may include monophasic or unidirectional and/or biphasic or bidirectional shock waveforms. Defibrillation may also include delivery of pulses over two current pathways.

Other ICD device may provide programmable low-energy cardioversion in addition to or in lieu of high-energy shocks (e.g., tier 512). Again, such lower tiered therapies are worth trying to conserve ICD energy and to minimize patient anxiety, pain or discomfort. In low-energy cardioversion, an ICD device typically delivers a cardioversion stimulus (e.g., 0.1 J, etc.) synchronously with a QRS complex; thus, avoiding the vulnerable period of the T wave and avoiding an increased risk of initiation of ventricular fibrillation. Yet other ICD devices provide for antitachycardia pacing (e.g., tier 508), which is typically a relatively painless scheme aimed at termination of monomorphic ventricular tachycardias.

Regarding antitachycardia pacing (e.g., tier 508), an ICD device may use a technique known as overdrive pacing, which is based on the observation that a mechanism of ventricular tachycardia involves re-entry, for example, a circulating wavefront of excitation within a discrete region of myocardium. Often, between the leading edge of the wavefront and the tail of refractoriness, just ahead of the circulating wavefront is a region known as an "excitable gap", which represents a segment of excitable myocardial tissue about to be depolarized by the propagating wavefront. Hence, the excitable gap circulates with the wave of excitation. According to overdrive pacing, an ICD device delivers a train of rapidly paced pulses to increase the probability of invasion of the excitable gap, for example, antitachycardia pacing can involve use of a burst of ventricular paced pulses (e.g., a burst of approximately 15 individual pulses). Burst pacing can optionally involve ramp pacing (e.g., decreasing temporal spacing of individual pulses in a burst with respect to time) and/or scanning (e.g., decreasing temporal spacing between bursts). Often, an ICD device uses antitachycardia pacing as a first tier of therapy, for example, in patients with ventricular tachycardia and a heart rate less than approximately 180 bpm. Again, if termination does not occur after ATP, then the ICD device may implement a more aggressive therapy (e.g., low-energy cardioversion, defibrillation).

Regarding implementation of various therapies, an ICD typically relies on sensing and/or detecting circuitry and/or algorithms to determine when a particular therapy is needed or desirable. A fundamental manner of identifying sustained ventricular tachycardia (VT) involves detecting a heart rate that exceeds a set value, for example, an episode of sustained VT may exhibit a rate in excess of 150 beats per minute (bpm). Other information is optionally used to distinguish a VT from a supraventricular tachycardia (SVT). Such other information can include identification of cycle length stability, abruptness of onset of the tachyarrhythmia, and duration of sustained rate. Regarding ventricular fibrillation (VF), rates in excess of approximately 240 bpm are not uncommon. An ICD, having appropriate defibrillation capabilities can respond to such rate accordingly with defibrillation or other therapy. Thus, with rates of approximately 150 bpm to approximately 230 bpm, antitachycardia pacing (e.g., tier 508) or low-energy cardioversion (e.g., tier 512) are optionally used; for rates greater than approximately 230 bpm, an ICD device may respond with defibrillation (e.g., tier 516). Of course, the set rates are optionally adjustable to account for patient characteristics. In addition, as described above, pacing therapy may be used (e.g., tier 504).

Another issue in ICD therapy involves a marked bradycardia following postconversion, which occurs in about 10% of patients successfully converted out of VT or VF. Thus, an ICD device may use backup pacing to prevent and/or minimize postconversion bradycardia.

While the foregoing discussion focuses primarily on ventricular conditions and ventricular therapies, tiered therapy also exists for atrial conditions. Atrial therapies may include atrial fibrillation therapies. AF suppression therapies generally request an increase atrial overdrive pacing rate only if a predetermined number of P-waves occur within a predetermined number of cycles. For example, a conventional AF suppression algorithm will request an increase in atrial overdrive pacing rate if two P-waves occur in 16 consecutive pacing cycles. In addition, the requested rate increase is typically based on a present pacing rate (e.g., 110% of the present rate).

Various exemplary devices and/or methods optionally disable analgesic stimulation based on occurrence of one or more conditions where analgesic stimulation would be detrimental or deplete device energy. For example, based on continuing experience, the organized tachycardia may respond to ATP therapy such that cardioversion or defibrillation shocks are not required. This is more likely to occur with slow tachycardias as contrasted with fast tachycardias. Another setting would be the third or fourth defibrillation shock. If the patient is still in fibrillation at this point, the patient is likely to be syncopal and effectively anesthetized. At that point, it would be reasonable to discontinue analgesic stimulation as that would only be an additional source of battery current drain when the system is repeatedly charging to high outputs to deliver a shock.

Probability of Success of a Therapy

At the time of implantation of an ICD or after some time of in situ operation of an ICD in a patient, various therapies are optionally assigned probabilities of success. In addition, the probabilities may depend on characteristics of sensed and/or detected information. A probability of success may be based on programmed information and/or patient history with respect to an applied therapy. As described further below, such probabilities are optionally used to determine an appropriate course of analgesic stimulation.

FIG. 6 shows an exemplary method 600 for assigning a probability to an applied therapy. In a detection block 604, an ICD detects a need for an initial therapy. For example, an ICD may detect a lengthening of an interval that is characteristic of, or a precursor to, an abnormal cardiac condition. Next, in a probability block 608, the ICD assigns or associates the therapy with a probability. For example, the ICD may determine that pacing, as an initial therapy, has previously been successful 15% of the time in terminating the lengthening and any subsequent worsened condition related to the lengthening. The method 600 may optionally determine, for example, on a cost-benefit basis, whether implementation of the therapy is worthwhile. If it is not worthwhile, then the ICD may select another therapy. In any case, in a delivery block 612, a selected therapy is delivered to the patient. A decision block 614 follows that determines whether the delivered therapy was successful. If the delivered therapy was successful, then the method terminates in an end block 616. However, if the delivered therapy was not successful, then the method 600 continues in a change therapy block 620 that changes the therapy, for example, to a higher tier of therapy. The probability block 608 follows wherein the probability assigned to the new therapy may account for a lack of success in the prior delivered therapy. For example, an ATP therapy may have a probability of success of approximately 50% if proceeded by an unsuccessful lower tier pacing therapy and a probability of success of approximately 40% if not proceeded by a lower tier therapy.

Variable Analgesic Stimulation

Various exemplary methods, devices and/or systems use analgesic stimulation to reduce or minimize patient pain or discomfort associated with therapies such as, but not limited to, cardioversion or defibrillation. Analgesic stimulation may occur with stimulation parameters that have a variable time course. The analgesic stimulation parameters may vary with respect to tier of therapy, probability of success of a therapy, number of times a therapy has been delivered, nature of cardiac condition, time of day, or a variety of other factors.

FIG. 7 shows an exemplary method 700 wherein one or more analgesic stimulation parameters vary with respect to the number of times a therapy has been delivered. The method 700 commences in a detection block 704 wherein a need for an initial therapy is detected (e.g., any particular therapy or tier of therapy). Next, in an analgesic stimulation block 708, analgesic stimulation is delivered with appropriate delivery parameters. Before, after, or simultaneous to delivery of analgesic stimulation a delivery block 712 initiates therapy delivery (e.g., antitachycardia pacing (ATP)). A decision block 716 follows wherein a decision is made as to whether the therapy was successful. If the delivered therapy was successful, then the method 700 terminates in an end block 720. If the delivered therapy was unsuccessful, then the method 700 continues in a limit check block 724, which determines whether a limit has been exceeded for the delivered therapy. For example, an antitachycardia pacing therapy tier may have a limit of three two minute periods. If the decision block 724 decides that the limit has been met or exceeded, whichever case may apply, then the method 700 continues in a change therapy block 728. The change therapy block 728 optionally calls for implementation of a higher tier of therapy (e.g., cardioversion or defibrillation shock) and optionally continues in the analgesic stimulation block 708 wherein analgesic stimulation occurs at the same or at different analgesic stimulation parameters as appropriate.

If the decision block 724 decides that the limit for the particular tier of therapy has not been exceeded or met, whichever case may apply, then the method 700 continues in the change analgesic stimulation parameter block 732. The change parameter block 732 may change any of a variety of analgesic stimulation parameters as appropriate. For example, the change block 732 may change analgesic stimulation power level, duty cycle, frequency, stimulation electrode or electrodes, forms of analgesic stimulation (e.g., TENS, SCS, electroacupuncture, etc.), etc. Further, the change block 732 may base any change in parameter at least in part on cardiac condition treated, probability of success of the therapy for the cardiac condition, ICD resources (e.g., power reserve, etc.), etc.

Yet further, the change parameter block 732 may provide for delays or changes in therapy parameters (e.g., changes in parameters in a particular tier of therapy). Any particular delay optionally allows for production of an analgesic effect by the analgesic stimulation. Again, some forms of analgesic stimulation have a more immediate analgesic effect when compared to other forms of analgesic stimulation.

FIG. 8 shows an exemplary method 800 wherein one or more analgesic stimulation parameters vary with respect to the number of times a therapy has been delivered and/or with respect to a probability of success of a therapy or therapies. The method 800 commences in a detection block 804 wherein a need for an initial therapy is detected (e.g., any particular therapy or tier of therapy). Next, in a probability block 806, the therapy is assigned or associated with a probability. For example, an ICD may determine that pacing, as an initial therapy, has previously been successful 15% of the time in terminating a particular cardiac condition and any subsequent worsened condition related to the lengthening. The method 800 may optionally determine, for example, on a cost-benefit basis, whether implementation of the therapy is worthwhile. If it is not worthwhile, then another therapy may be selected. In any case, a therapy is selected based on the probability of success.

Next, in an analgesic stimulation block 808, analgesic stimulation is delivered with appropriate delivery parameters. Before, after, or simultaneously to analgesic stimulation a delivery block 812 initiates delivery of a selected therapy. A decision block 816 follows wherein a decision is made as to whether the therapy was successful. If the delivered therapy was successful, then the method 800 terminates in an end block 820. If the delivered therapy was unsuccessful, then the method 800 continues in a limit check block 824, which determines whether a limit has been exceeded for the delivered therapy. For example, an antitachycardia pacing therapy tier may have a limit of three two minute periods. If the decision block 824 decides that the limit has been met or exceeded, whichever case may apply, then the method 800 continues in a change therapy block 828. The change therapy block 828 optionally calls for implementation of a higher tier of therapy and optionally continues in the probability block 806 wherein the therapy is assigned or associated with an appropriate probability of success. The analgesic stimulation block 808 may stimulate at the same or at different analgesic stimulation parameters as appropriate.

If the decision block 824 decides that the limit for the particular therapy has not been exceeded or met, whichever case may apply, then the method 800 continues in an update probability of success block 830. For example, if a first delivery of a therapy fails, then the probability of success for a second delivery may differ (e.g., within appropriate limits, etc.). In particular, the probability for a second delivery may be less than that for the first delivery and that of a third delivery may be less than that of the first or second deliveries. Such information is optionally used in a change analgesic stimulation parameter block 832 to change one or more analgesic stimulation parameters. For example, given the scenario of lessened probability of success for a second delivery, the analgesic stimulation level may be increased, especially if the change therapy block 828 calls for a therapy that may cause patient pain or discomfort. For example, if the present therapy is ATP and the next therapy to be implemented includes a defibrillation shock, then it may be more probable than not that the ATP therapy will fail and that defibrillation will be called for. Early and aggressive analgesic stimulation may help minimize patient pain or discomfort associated with a probable defibrillation shock.

In general, the change parameter block 832 may change any of a variety of analgesic stimulation parameters as appropriate. For example, the change block 832 may change analgesic stimulation power level, duty cycle, frequency, stimulation electrode or electrodes, forms of analgesic stimulation (e.g., TENS, SCS, electroacupuncture, etc.), etc. Further, the change block 832 may base any change in parameter at least in part on cardiac condition treated, probability of success of the therapy for the cardiac condition, ICD resources (e.g., power reserve, etc.), etc.

Yet further, the change parameter block 832 may provide for delays or changes in therapy parameters (e.g., changes in parameters in a particular tier of therapy). Any particular delay optionally allows for production of an analgesic effect by the analgesic stimulation. Again, some forms of analgesic stimulation have a more immediate analgesic effect when compared to other forms of analgesic stimulation.

While various exemplary methods aim to cause an analgesic effect prior to therapy such as defibrillation shock, such methods are optionally used to cause an analgesic effect in instances where an implantable cardiac therapy device delivers a stimulus in excess of approximately 100 mJ or greater than 1 mJ or 10 mJ above a typical pacing energy. In general, analgesic stimulation may be beneficial anytime antiarrhythmia therapy would cause a patient to feel a sensation.

Exemplary Analgesic Stimulation Devices

An exemplary device for analgesic stimulation includes an SVC coil capable of delivering analgesic stimulation (e.g., in conjunction with a can) and an RV coil capable of delivering a cardioversion and/or a defibrillation shock (e.g., in conjunction with a can). This exemplary device may also include one or more electrodes capable of sensing cardiac information (e.g., atrial and/or ventricular information).

Such a device is optionally programmable to perform various exemplary methods presented herein and/or other methods.

Another exemplary device for analgesic stimulation includes an SVC coil capable of delivering analgesic stimulation (e.g., in conjunction with a can) and bipolar sensing electrodes capable of sensing cardiac information (e.g., atrial and/or ventricular information). This exemplary device may also include one or more electrodes capable of delivering a cardioversion and/or a defibrillation shock. Such a device is optionally programmable to perform various exemplary methods presented herein and/or other methods.

Yet another exemplary device for analgesic stimulation includes one or more electrodes capable of delivering analgesic stimulation to a spinal cord, to a vagus nerve, and/or to an acupoint. This exemplary device may also include one or more electrodes capable of delivering a cardioversion and/or a defibrillation shock. This exemplary device may also include one or more electrodes capable of sensing cardiac information (e.g., atrial and/or ventricular information). Such a device is optionally programmable to perform various exemplary methods presented herein and/or other methods.

Conclusion

Although exemplary methods and/or devices have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods and/or devices.

What is claimed is:

1. A method for treating a cardiac condition, the method comprising:
    delivering analgesic stimulation and a first antitachycardia therapy to a patient;
    determining whether the first antitachycardia therapy successfully treated the cardiac condition;
    changing one or more analgesic stimulation parameters if the first antitachycardia therapy failed to treat the cardiac condition; and
    delivering analgesic stimulation based on the one or more changed analgesic stimulation parameters and a second antitachycardia therapy to the patient if the first antitachycardia therapy failed to treat the cardiac condition, wherein the second antitachycardia therapy is different from the first antitachycardia therapy.

2. The method of claim 1 wherein the first antitachycardia therapy comprises a ventricular therapy.

3. The method of claim 1 wherein the first antitachycardia therapy comprises an atrial therapy.

4. The method of claim 1 wherein the cardiac condition comprises a precursor to arrhythmia.

5. The method of claim 1 wherein the cardiac condition comprises a precursor to fibrillation.

6. The method of claim 1 wherein the cardiac condition comprises arrhythmia.

7. The method of claim 1 wherein delivering analgesic stimulation comprises delivering electroacupuncture stimulation.

8. The method of claim 1 wherein delivering analgesic stimulation comprises delivering transcutaneous electrical stimulation (TENS).

9. The method of claim 1 wherein delivering analgesic stimulation comprises delivering spinal cord stimulation (SCS).

10. The method of claim 1 wherein determining comprises sensing cardiac information.

11. The method of claim 10 wherein sensing cardiac information comprises using one or more electrodes implanted in an atrial or a ventricular chamber.

12. The method of claim 1 wherein the second antitachycardia therapy is a higher tier therapy than the first antitachycardia therapy.

13. The method of claim 12 wherein the higher tier therapy comprises defibrillation therapy.

14. A method comprising:
    detecting a need for a therapy selected from tiered therapies that include cardioversion and/or defibrillation therapies wherein the delivered therapy aims to treat a cardiac condition;
    assigning a probability of success to the therapy; and
    determining one or more analgesic stimulation parameters based at least in part on the probability.

15. The method of claim 14 wherein the therapy comprises antitachycardia therapy.

16. The method of claim 14 wherein the therapy comprises a ventricular therapy.

17. The method of claim 14 wherein the cardiac condition comprises a precursor to arrhythmia.

18. The method of claim 14 wherein the analgesic stimulation comprises transcutaneous electrical stimulation (TENS).

19. The method of claim 14 further comprising delivering the therapy and determining whether the therapy successfully treated the cardiac condition.

20. An implantable device for treating a cardiac condition comprising:
    means for delivering analgesic stimulation and a first antitachycardia therapy;
    means for determining whether the first antitachycardia therapy successfully treated the cardiac condition;
    means for changing one or more analgesic stimulation parameters if the first antitachycardia therapy did not successfully treat the cardiac condition; and
    means for delivering analgesic stimulation based on the one or more changed analgesic stimulation parameters and a second antitachycardia therapy if the first antitachycardia therapy did not successfully treat the cardiac condition, wherein the second antitachycardia therapy is different from the first antitachycardia therapy.

21. The device of claim 20, wherein the means for delivering a therapy includes a programmable pulse generator and a lead having one or more electrodes capable of being positioned to deliver a cardiac stimulation pulse.

22. An implantable cardiac system for treating a cardiac condition, the system comprising:
    at least one lead configured for implant within a patient and comprising at least one electrode;
    circuitry connected to the at least one lead and operative to generate electrical pulses for delivery to the patient;
    an analgesic stimulation device operative to generate analgesic stimulation for delivery to the patient; and
    a controller connected to the circuitry and the analgesic stimulation device, the controller being operative to control the analgesic stimulation device to generate analgesic stimulation and to control the circuitry to generate a first antitachycardia therapy during a first phase, wherein the controller is connected to the at least one lead and operative to determine whether the first antitachycardia therapy successfully treated the cardiac condition, wherein the controller is further operative to change one or more analgesic stimulation parameters if the first antitachycardia therapy failed to treat the cardiac condition and to control the analgesic stimulation device to generate analgesic stimulation based on the one or more changed analgesic stimulation parameters and to control the circuitry to generate a second antitachycardia therapy different from the first antitachycardia therapy if the first antitachycardia therapy failed to treat the cardiac condition.

23. The system of claim 22 wherein the circuitry comprises a pulse generator that is operative to generate stimulation pulses.

24. The system of claim 22 wherein the circuitry comprises a shocking circuit that is operative to generate at least one of cardioversion and defibrillation pulses.

25. The system of claim 22 wherein the analgesic stimulation device is connected to the at least one electrode for delivery of analgesic stimulation to the patient.

26. The system of claim 22 wherein the analgesic stimulation device is operative to deliver at least one of electroacupuncture stimulation, transcutaneous electrical stimulation (TENS), and spinal cord stimulation (SCS).

27. A method for treating a cardiac condition, the method comprising:

delivering analgesic stimulation and antitachycardia therapy to a patient;

determining whether the antitachycardia therapy successfully treated the cardiac condition;

changing one or more analgesic stimulation parameters if the antitachycardia therapy failed to treat the cardiac condition; and delivering analgesic stimulation based on the one or more changed analgesic stimulation parameters to the patient and the antitachycardia therapy to the patient if the antitachycardia therapy failed to treat the cardiac condition.

* * * * *